United States Patent
Patterson et al.

(10) Patent No.: US 8,100,859 B2
(45) Date of Patent: Jan. 24, 2012

(54) BENT OBTURATOR

(75) Inventors: Donald Patterson, Bloomington, IN (US); Sharon M. Huff, Jeffersonville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/145,232

(22) Filed: Jun. 24, 2008

(65) Prior Publication Data

US 2009/0318870 A1    Dec. 24, 2009

(51) Int. Cl.
    *A61M 5/178*    (2006.01)
(52) U.S. Cl. ................................... 604/164.01
(58) Field of Classification Search .......... 604/164.01, 604/170.03, 170.02, 166.01, 164.13
    See application file for complete search history.

(56) References Cited

U.S. PATENT DOCUMENTS

| | | | |
|---|---|---|---|
| 3,867,945 A | 2/1975 | Long | |
| 4,808,168 A * | 2/1989 | Warring | 604/158 |
| 5,250,035 A * | 10/1993 | Smith et al. | 604/168.01 |
| 5,263,936 A | 11/1993 | Yurino | |
| 5,300,084 A * | 4/1994 | Johnson | 606/185 |
| 5,334,185 A | 8/1994 | Giesy et al. | |
| 5,512,052 A * | 4/1996 | Jesch | 604/158 |
| 5,669,882 A | 9/1997 | Pyles | |
| 5,807,339 A | 9/1998 | Boström et al. | |
| 5,891,057 A | 4/1999 | Chaisson et al. | |
| 5,908,413 A * | 6/1999 | Lange et al. | 604/529 |
| 6,245,029 B1 | 6/2001 | Fujita et al. | |
| 6,254,611 B1 | 7/2001 | Vrba | |
| 7,001,361 B2 | 2/2006 | Polidoro | |
| 2002/0052641 A1 | 5/2002 | Monroe et al. | |
| 2004/0243061 A1 | 12/2004 | McGurk | |
| 2006/0064062 A1 | 3/2006 | Gurusamy et al. | |
| 2006/0135915 A1 | 6/2006 | Tucker | |
| 2007/0142842 A1 | 6/2007 | Krueger et al. | |

FOREIGN PATENT DOCUMENTS

WO    WO 94/27697    12/1994

* cited by examiner

*Primary Examiner* — Kevin C. Sirmons
*Assistant Examiner* — Brandy C Scott
(74) *Attorney, Agent, or Firm* — Brinks Hofer Gilson & Lione (57) ABSTRACT

A catheter-insertion assembly includes a catheter with a proximal end and a distal end, a needle with a proximal end and a beveled distal end forming a sharp distal point, and an obturator with a proximal end and a distal end. The distal end of the obturator includes at least one bend. The bend allows the distal end of the obturator to protect the catheter from the sharp distal point of the needle during insertion of the needle through the catheter.

15 Claims, 4 Drawing Sheets

BENT OBTURATOR

BACKGROUND

Drainage catheters are used to drain excess fluid from the body of a patient. For example, drainage catheters may be suitable for draining abscesses, biliary system fluids, excess peritoneal fluid (ascites), and the urinary tract.

Drainage catheters are often made of flexible materials such as polyurethane, polytetrafluoroethylene (PTFE), or any other material known in the art. The distal end of a drainage catheter may be tapered, slightly beveled or blunt. The use of a flexible material and a tapered, slightly beveled distal or blunt end minimizes damage to the patient's tissue while the catheter is in place. The distal end of a drainage catheter is also frequently curved to prevent the distal end of the catheter from moving once placed in the desired location in a patient's body. This curve is called a "pig-tail."

In order to drain excess fluid, the catheter must be inserted into the body of a patient at the desired location. The catheter itself is generally inserted into the body through an incision. The incision is often made by first nicking the skin with a sharp instrument such as a scalpel and then pushing a needle or cannula through the opening formed by that nick. The process of inserting the catheter is accomplished by inserting a needle through the catheter until the sharp distal end of the needle protrudes beyond the distal end of the catheter. The needle and catheter are then pushed through the nick in the patient's skin and into the body until they reaches the site of the fluid to be drained. Once in place, the needle is withdrawn through the drainage catheter so that it is no longer protruding beyond the distal end of the catheter. The catheter may then be used to drain the fluid. The withdrawal of the sharp needle into the body of the catheter prevents accidental pricking or irritation to the patient.

When the needle or cannula is threaded through the lumen of the catheter prior to insertion of the drainage catheter, there is a risk that the sharp distal end of the needle or cannula will damage the interior of the catheter. There is a particularly high risk of a needle damaging drainage catheters having a curved "pig-tail" at the distal end. The needle may puncture the catheter or "shave" the interior walls of the catheter. It is undesirable to "shave" the interior of the catheter wall because this weakens the catheter. In addition, the fine shavings produced by this damage may result in blockage to the drainage catheter. The shavings may also make their way into the patient.

In order to prevent damage to the interior of the drainage catheter, an obturator with a rounded distal end is often inserted into the lumen of the needle or cannula before the needle is threaded through the catheter. Obturators known in the art are typically straight and have a rounded distal end. An obturator is generally inserted through the lumen of the needle or cannula so that the rounded distal end of the obturator is distal to the distal end of the needle or cannula. Once the obturator is in place, the obturator-needle assembly may be threaded through the lumen of the drainage catheter. The rounded distal end of the obturator attempts to protect the interior of the drainage catheter from being damaged by the sharp distal end of the needle.

Despite the use of obturators in the prior art, "shaving" of the interior of the catheter still occurs in some instances.

BRIEF SUMMARY

A catheter-insertion assembly is described. The assembly includes a catheter with a proximal end and a distal end, a needle with a proximal end and a beveled distal end forming a sharp distal point, and an obturator with a proximal end and a distal end. The distal end of the obturator includes at least one bend. The bend allows the distal end of the obturator to protect the catheter from the sharp distal point of the needle during insertion of the needle through the catheter. This may reduce the risk of the needle damaging, e.g., puncturing or shaving, the interior of the catheter.

The invention may include any of the following aspects in various combinations and may also include any other aspect described below in the written description or in the attached drawings.

One embodiment of a catheter-insertion assembly comprises:
a catheter having a proximal end, a distal end and an inner lumen extending from the proximal end to the distal end;
a needle having a proximal end and a beveled distal end forming a sharp distal point, the needle also having a length and an inner lumen having a diameter;
an obturator having a proximal end and a distal end, the obturator having a diameter that is smaller than the inner diameter of the needle, and a length that is greater than the length of the needle;
a proximal bend in the distal end of the obturator; and
a distal bend in the distal end of the obturator located distally to the proximal bend, the distal bend being angled opposite the proximal bend such that the proximal bend and the distal bend are in a single plane,
wherein the obturator is positioned within the lumen of the needle, and the needle is positioned within the lumen of the catheter, and wherein the obturator is capable of protecting the inner lumen of the catheter from being damaged by the needle.

Another embodiment comprises a catheter-insertion assembly wherein the proximal bend in the distal end of the obturator includes a concave side and a convex side, and the obturator is positioned such that the concave side of the proximal bend is substantially angularly aligned with the sharp distal point of the beveled distal end of the needle.

Another embodiment comprises a catheter-insertion assembly wherein the obturator is sized approximately two gauges smaller than the needle.

Another embodiment comprises a catheter-insertion assembly wherein the distal end of the catheter is curved.

Another embodiment comprises a catheter-insertion assembly further comprising a pigtail straightener.

Another embodiments comprises catheter-insertion assembly wherein the obturator is metal.

Another embodiment according to the disclosure comprises a catheter-insertion assembly wherein the distance between the proximal bend and the distal bend in the distal end of the obturator is approximately equal to the diameter of the inner lumen.

Another embodiment according to the disclosure comprises a catheter-insertion assembly wherein the proximal bend in the distal end of the obturator is positioned approximately 2 millimeters distally from the sharp distal point of the beveled distal end of the needle.

Another embodiment comprises a catheter-insertion assembly wherein the distal bend in the distal end of the obturator is positioned approximately 3.5 millimeters distally from the sharp distal point of the beveled distal end of the needle.

Another embodiment comprises a catheter-insertion assembly wherein the beveled distal end of the needle includes a back bevel.

Another embodiment comprises a catheter-insertion further comprising a means for positioning the obturator within the needle such that the concave side of the proximal bend of the obturator is substantially angularly aligned with the sharp distal point of the needle.

Another embodiment comprises a catheter-insertion further comprising a notch in the proximal end of the needle;

a tab on the proximal end of the obturator, wherein the tab is sized to fit inside the notch, and the notch and tab are positioned so that when the tab is fit inside the notch, the concave side of the proximal bend of the obturator is substantially angularly aligned with the sharp distal point of the needle.

An embodiment of an obturator suitable for protecting the interior of a catheter from a needle comprises:

an elongate member having a distal end and a proximal end, the distal end having a rounded most distal point;

a proximal bend located proximal to the rounded most distal point; and a distal bend located between the proximal bend and the rounded most distal point of the elongate member, the distal bend being angled opposite the proximal bend such that the distal bend and the proximal bend are in a single plane, the distal bend and the elongate bend making the elongate member being capable of protecting the interior of a catheter from being damaged by a needle.

Another embodiment comprises an obturator wherein the length of the obturator between the distal bend and the rounded most distal point is approximately 0.5 millimeters.

Another embodiment comprises an obturator wherein the magnitude of the angle forming the proximal bend is substantially the same as the magnitude of the angle forming the distal bend.

Another embodiment comprises an obturator wherein the magnitude of the angle forming the proximal bend is approximately 178.5° and the magnitude of the angle forming the distal bend is approximately 178.5°.

Another embodiment of a catheter-insertion assembly according to the disclosure comprises:

a catheter having a proximal end, a distal end, and an inner lumen extending from the proximal end to the distal end;

a needle having a proximal end and a beveled sharp distal end forming a sharp distal point, the needle also having a length and an inner lumen having a diameter;

an obturator having a proximal end and a distal end, the obturator having a diameter less than the diameter of the inner lumen, and having a length greater than the length of the needle; and a bend in the distal end of the obturator, the bend having a concave side and a convex side, the bend being positioned so that the concave side is substantially aligned with the sharp distal point of the needle, wherein the obturator is positioned within the lumen of the needle and the needle is positioned within the lumen of the catheter, and wherein the obturator is capable of protecting the inner lumen of the catheter from being damaged by the needle.

Another embodiment comprises a catheter-insertion assembly wherein the obturator is at least two gauges smaller than the needle.

Another embodiment comprises a catheter-insertion assembly wherein the bend is positioned approximately 2 millimeters distally of the sharp distal point of the needle.

Another embodiment comprises a catheter-insertion assembly wherein the beveled distal end of the needle includes a back bevel.

DETAILED DESCRIPTION OF THE DRAWINGS AND THE PRESENTLY PREFERRED EMBODIMENTS

Figure 1:
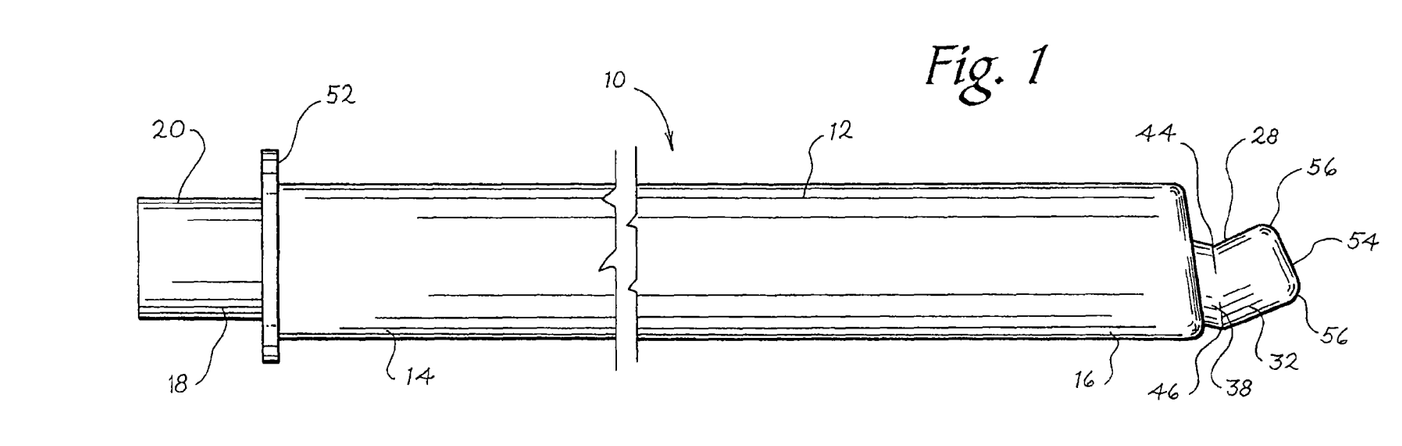
FIG. 1 is a perspective view of an embodiment of the catheter-insertion assembly.

Referring now to the drawings, and particularly to FIG. 1, a catheter-insertion assembly 10 is shown. In the present application, the term "proximal" refers to the direction that is generally toward a physician during a medical procedure, while the term "distal" refers to a direction that is generally towards a target site within a patient's anatomy during a medical procedure.

The catheter insertion assembly 10 includes a catheter 12 having a proximal end 14, a distal end 16, and an interior surface defining a lumen extending from the proximal end 14 to the distal end 16.

Figure 2:
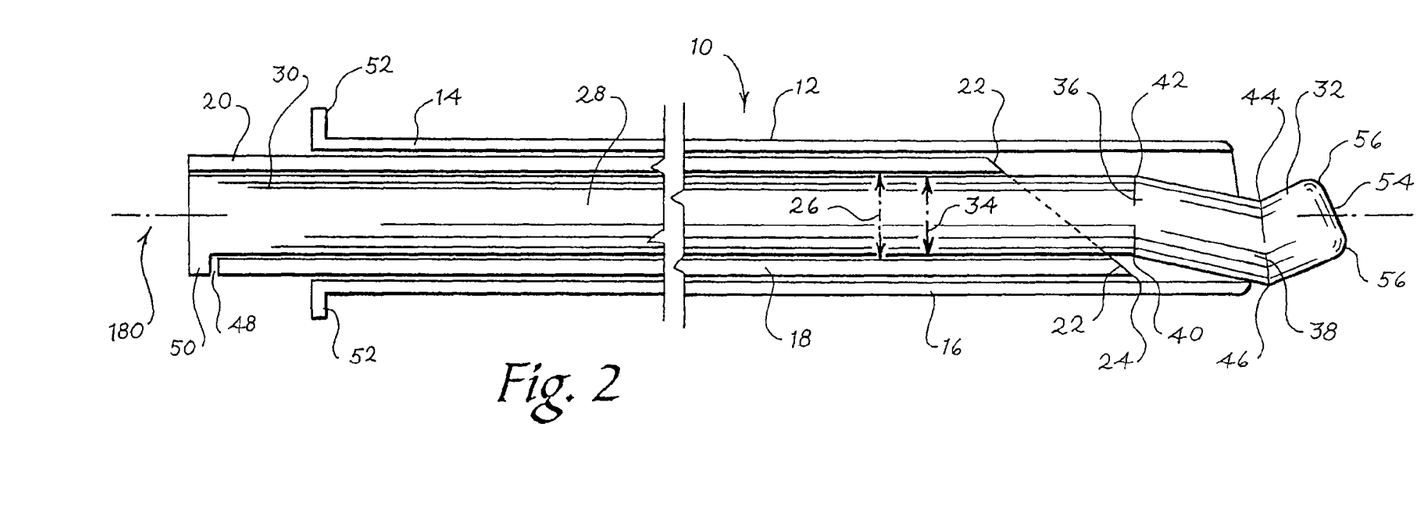
FIG. 2 is a side cross-sectional view of the catheter-insertion assembly of FIG. 1 in which the obturator is in an extended position.

FIG. 2 shows a side cross-sectional view of the catheter-insertion assembly 10 of FIG. 1. FIG. 2 illustrates that a needle 18 having a proximal end 20 and a beveled distal end 22 may be positioned concentrically within the catheter 12. The beveled distal end 22 of the needle 18 forms a sharp distal point 24. An obturator 28 is positioned concentrically inside the needle 18. The obturator 28 is formed of an elongate member and has a proximal end 30 and a distal end 32. The diameter 34 of the obturator 28 is less than the inner diameter 26 of the needle 18, which allows the obturator 28 to fit concentrically within the needle 18. The length of the obturator 28 is greater than the length of the needle 18 to allow the distal end 32 of the obturator 28 to be extended so that it is distal to the distal end 22 of the needle 18, including the sharp distal point 24 of the needle 18.

The distal end 32 of the obturator 28 of the catheter-insertion assembly 10 shown in FIGS. 1 and 2 has a proximal bend 36 and a distal bend 38. The proximal bend 36 has a concave side 40 and a convex side 42. Likewise, the distal bend 38 has a concave side 44 and a convex side 46. The distal bend 38 is located distally to the proximal bend 36. The distal bend 38 is angled opposite to the proximal bend 36 such that the proximal bend 36 and the distal bend 38 are located within a single plane. Thus, the distal end 32 of the obturator 28 has a generally zigzag configuration.

FIG. 2 illustrates that the three components of the catheter insertion assembly 10—the obturator 28, the needle 18, and the catheter 12—may be assembled to have a substantially coaxial relationship. In this embodiment, the needle 18 and catheter 12 have a common central longitudinal axis 180. As shown in FIG. 2, the portion of the obturator 28 proximal to the proximal bend 36 generally may share this same common central longitudinal axis. As illustrated in FIG. 2, a particular feature of the obturator 28, e.g., the convex side 46 of the distal bend 38, may be angularly aligned along this central longitudinal axis 180 with a particular feature of the needle 18, e.g. the sharp distal point 24 of the needle 18. In FIG. 2, the convex side 46 of the distal bend 38 and the sharp distal point 24 of the needle 18 share the same angle about the central longitudinal axis 180 of the assembly 10. Therefore, the convex side 46 of the distal bend 38 is angularly aligned with the sharp distal point 24 of the needle 18 in FIG. 2.

It is preferable that the desired angular alignment of particular features of the obturator 28 and the needle be maintained throughout the course of a medical procedure. Thus, it is preferable that the needle and obturator not be rotated relative to one another during use. This insures that the desired angular alignment of the features of the needle relative to the obturator is maintained throughout the procedure. For embodiments involving the use of a curved catheter 12, it may also be preferable to keep the sharp distal point 24 of the needle 18 angularly aligned relative to part of the curve of the catheter 12. Although particular features of the obturator 28 and needle 18 should maintain the desired angular alignment, the features may move relative to one another in the longitudinal direction during use, thereby changing the longitudinal relationship between two features. For example, FIG. 2 shows the convex side 46 of the distal bend 38 located distal to the sharp distal point 24 of the needle 18. In contrast, the convex side 46 of the distal bend 38 is located proximal to the sharp distal point 24 of the needle 18 in FIG. 3. Although the convex side 46 of the distal bend 38 changes in longitudinal position relative to the sharp distal point 24 of the needle 18 between FIGS. 2 and 3, the angular alignment of the two features is maintained in both FIGS. 2 and 3.

As shown in FIG. 2, it is preferable that the proximal bend 36 of the obturator 28 is angularly angled such that the concave side 40 of the proximal bend 36 is angularly aligned with the sharp distal point 24 of the needle 18. In this configuration, therefore, the convex side 42 of the proximal bend 36 faces the side of the catheter insertion assembly 10 diametrically opposite to the sharp distal point 24 of the needle 18. As previously noted, it is also preferable that the distal bend 38 be positioned so that the convex side 46 of the distal bend 38 of the obturator 28 is angularly aligned with the sharp distal point 24 of the needle 18. In this preferred embodiment, the proximal bend 36 and the distal bend 38 form a zig-zag-like configuration.

In other embodiments having a double bend, the bends may not form a zig-zag-like configuration. In these embodiments, the distal bend 38 of the obturator 28 may not bend in the opposite direction as the proximal bend 36. In still other embodiments, the distal bend 38 in conjunction with the proximal bend 36 of the obturator 28, may form a zig-zag-like configuration, but the convex side 46 of the distal bend 38 may not be angularly aligned with the sharp distal point 24 of the needle 18.

In embodiments having an obturator 28 with a concave side 40 of the proximal bend 36 and the convex side of the distal bend 38 angularly aligned with the sharp distal point 24 of the needle 18, a notch 48 and tab 50 may be used to facilitate positioning the obturator 28 relative to the needle 18. A notch 48 may be located in the proximal end 20 of the needle 18. The notch 48 is preferably angularly aligned with the sharp distal point 24 of the needle 18. A tab 50 configured to fit within the notch 48 may be located on the proximal end 30 of the obturator 28. The tab 50 is preferably angularly aligned with the convex side 46 of the distal bend 38 of the obturator 28. In use, the tab 50 on the obturator 28 fits into the notch 48 in the needle 18 causing the needle to be aligned with the obturator 28 so that the concave side 40 of the proximal bend 36 and convex side 46 of the distal bend 38 are angularly aligned with the sharp distal point 24 of the needle 18. Alternatively, a tab may be located on the needle and the notch may be located on the obturator.

A tab and notch may be located at any point on or around the needle 18 and obturator 28 so long as they allow the needle 18 and obturator 28 to be aligned as desired. Other means for positioning an obturator within a needle may be used, including the use of a slot with a tab, a knob, a flange, a luer fitting, or a visible indicia or marking on or near the proximal end of the needle and/or the obturator that would allow a person of ordinary skill to visibly confirm that the needle and obturator are aligned as desired. Any of the foregoing mechanisms may be used on the needle or obturator or both the needle and obturator. A combination of any such mechanisms may also be used to position the needle and obturator relative to one another.

The proximal end of the catheter 12 shown in FIGS. 1 and 2 features a male luer fitting 52. This male luer fitting 52 may enable the catheter 12 of the embodiment shown in FIGS. 1 and 2 to be easily attached to a female luer fitting on another device. The proximal end of the catheter 12 may feature any other feature for connecting the catheter 12 to another device known in the art. In other embodiments, the proximal end 14 of the catheter 12 may lack any feature adapted for connecting the catheter 12 to another device.

The catheter-insertion assembly 10 illustrated in FIGS. 1 and 2 is useful for inserting a needle 18 through a catheter 12 while minimizing or entirely avoiding damage to the catheter. In particular, the catheter-insertion assembly 10 may reduce the risk of the needle shaving the interior of the catheter. During use, the obturator 28 is inserted into the needle 18. As shown in FIG. 2, the distal end 32 of the obturator 28 preferably is positioned distally to the distal end 22 of the needle 18. Once positioned in this manner, the needle-obturator assembly is inserted through the proximal end 14 of the catheter 12. As the needle-obturator assembly are inserted into the catheter 12, the proximal bend 36 of the obturator 28 serves to distance the obturator 28 from the beveled distal end 22 of the needle. The convex side 46 of the distal bend 38 in the distal end 32 of the obturator 28 preferably contacts the interior surface of the catheter 12 a short distance distal to the sharp distal point 24 of the needle 18. Thus, as the needle-obturator assembly is slid through the catheter 12, the convex side 46 of the distal bend 38 of the obturator 28 pushes the inner wall of the catheter 12 away from the sharp distal point 24 of the needle 18. This prevents the sharp distal point 24 of the needle 18 from contacting the inner wall of the catheter 12 and thus reduces the risk of puncturing the catheter 12 or shaving the interior surface of the catheter 12.

The catheter-insertion assembly may also help prevent the obturator 28 from damaging the needle 18. The bend in the obturator 28 keeps the obturator from contacting the beveled distal end 16 of the needle 18, thereby preventing the obturator 28 from damaging or dulling the beveled distal end 22 of the needle 18.

As explained above, during the insertion of the needle 18 into the catheter 12 prior to a medical procedure, the distal end 32 of the obturator 28 is maintained distal to the needle 18 until the beveled distal end 22 of the needle 18 extends beyond the distal end 16 of the catheter 12. However, during a medical procedure, the obturator 28 and needle 18 may be slid distally and proximally within the catheter 12 as desired. Thus, a user may change the location of the distal end 32 of the obturator 28 and the distal end 22 of the needle 18 relative to one another and relative to the catheter 12 during a medical procedure.

Figure 3:
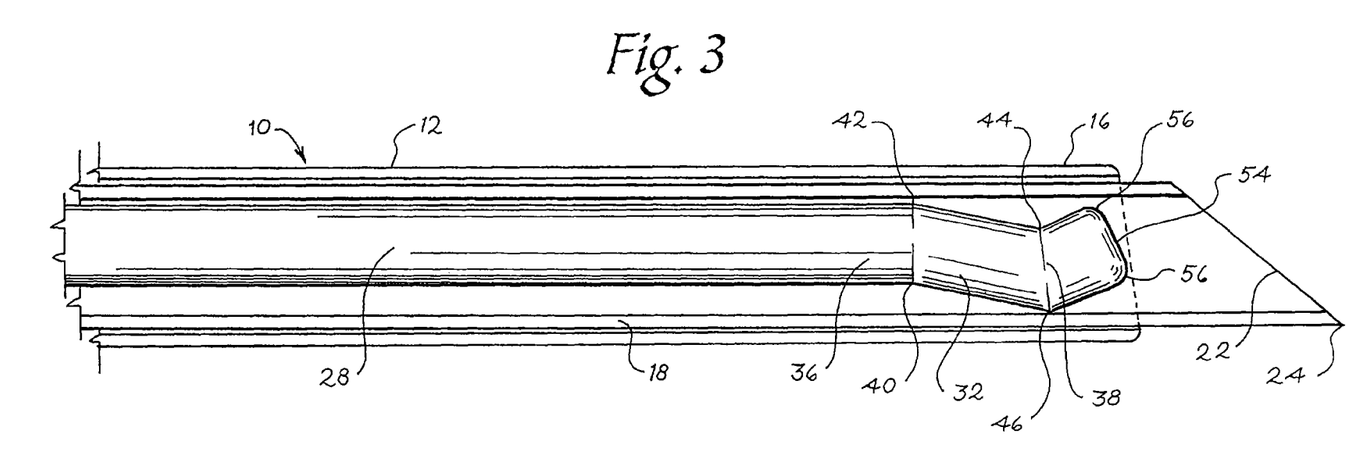
FIG. 3 is a partial side cross-sectional view of the catheter-insertion assembly of FIG. 1 in which the obturator is in a retracted position.

FIG. 3 shows the catheter-insertion assembly 10 of FIGS. 1 and 2 with the obturator 28 positioned for insertion of the assembly 10 into a patient. As shown in FIG. 3, when the distal end 22 of the needle 18 is clear of the distal end 16 of the catheter 12, the obturator 28 preferably is withdrawn into the needle 18 so that the distal end 32 of the obturator 28 is proximal to the beveled distal 22 of the needle 18. The beveled distal end 22 of the needle 18 is thus exposed. This allows the needle 18 to be used to make a puncture into the tissue of a patient. Alternatively, the needle may be used to facilitate the incision of the catheter-insertion assembly through an incision made by nicking the skin with a scalpel. The catheter 12 follows the needle 18 through the incision.

Once the catheter 12 is positioned in a patient as desired, both the needle 18 and obturator 28 may be withdrawn through the proximal end 14 of the catheter 12. In order to prevent the sharp distal point 24 of the needle 18 from puncturing the catheter 12 or shaving the interior wall of the catheter 12 during withdrawal, it may be preferable to extend the obturator 28 so that the distal end 32 of the obturator 28 is located distally to the distal end 22 of the sharp distal point 24 of the needle 18. This allows the obturator 28 to protect the catheter 12 from the needle 18 during withdrawal. The needle 18 and obturator 28 may be withdrawn only partially out of the catheter 12 or withdrawn entirely through the proximal end 14 of the catheter 12. In some embodiments it may be preferable to leave the obturator 28 within the catheter 12 in order to provide support to the catheter 12 during a medical procedure.

In many embodiments having a wide angle forming the proximal bend 36 and a distal bend 38, such as the embodiments shown in FIGS. 2 and 3, it may be preferable that the distance between the proximal bend 36 and the distal bend 38 is approximately equal to the inner diameter 26 of the needle 18. For embodiments having a wide angle, this distance may provide for a good working fit given the inner diameter of the needle and the outer diameter of the obturator. This distance may also be advantageous because it may ensure that the distal bend 38 protrudes sufficiently far to push the interior wall of the catheter 12 angularly aligned with the sharp distal point 24 of the needle 18 out of the path of the sharp distal point 24 of the needle 18. Other embodiments may feature a distance between the proximal bend 36 and the distal bend 38 that is less than the inner diameter 26 of the needle 18. Still other embodiments may have a distance between the proximal 36 and distal bends 38 that is substantially greater than the inner diameter 26 of the needle 18.

During the insertion of the needle 18 through the catheter 12, it is preferable that the proximal bend 36 of the obturator 28 be positioned so that it is approximately 2 millimeters distal to the sharp distal point 24 of the needle 18. This distance is believed to reduce the occurrence of catheter shavings during insertion of the needle 18. It is also believed that when catheter shavings do occur, this distance reduces the number and size of catheter shavings produced during insertion of the needle 18. In this embodiment it is preferable that the distal bend 38 of the obturator 28 be positioned so that it is approximately 3.5 millimeters distal to the sharp distal point 24 of the needle 18. It may be preferable to position the obturator so that the total extension of the obturator 28 beyond the most distal point 24 of the needle 18 is between 5 millimeters and 6 millimeters. However, the total length of the obturator 28 may also vary based on the size of the needle 18 and obturator 28 used.

In other embodiments, the distance between the sharp distal point 24 of the needle 18 and the proximal bend 36 of the obturator 28 may be approximately 1 millimeter, 3 millimeters, or any other suitable distance. However, it may be desirable to position the obturator 28 so that the proximal bend 36 is not too distal to the sharp distal point 24 of the needle 18 in order to ensure that the double bends may effectively work to hold the interior catheter 12 wall away from the sharp distal point 24.

In other embodiments, the sharp distal point 24 of the needle 18 and the concave side 40 of the proximal bend 36 may be positioned so that they are substantially longitudinally aligned during insertion of the needle through the catheter. In these embodiments, the convex side 42 of the proximal bend 36 will be substantially diametrically opposite to the sharp distal point 24 of the needle.

The length of the obturator 28 distal to the distal bend 38 is preferably approximately 0.5 millimeters. However, the length of the obturator 28 from the distal bend 38 to the most distal point 54 of the obturator 28 may vary. Although any other length may be used, it may be advantageous for the length of the obturator 28 distal to the distal bend 38 to be relatively small. This prevents the very distal end of the obturator from interfering with the way that the double bends of the obturator work to push the catheter wall out of the way of the sharp distal point 24 of the needle 18.

Figure 4:
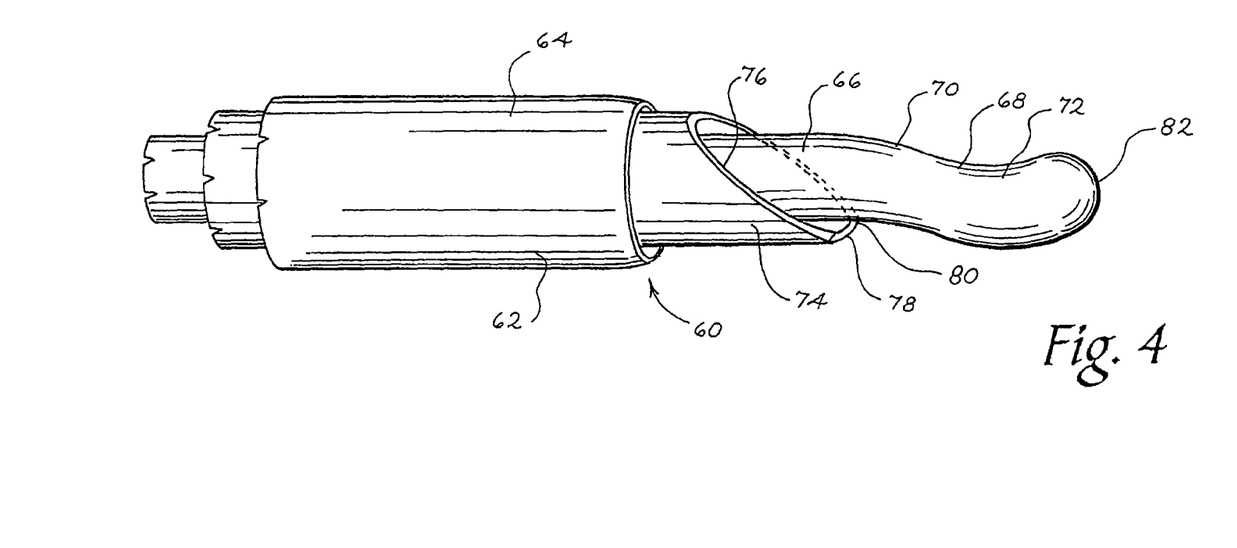
FIG. 4 is a partial perspective view of another embodiment of a catheter-insertion assembly.

The most distal point 54 of the obturator 28 may be rounded as shown in FIGS. 1, 2, and 3. The obturator 28 preferably has rounded edges 56 to prevent the obturator 28 from damaging the interior of the needle 18 and the catheter 12. This shape may also facilitate easy movement of the obturator 28 through the needle 18 and the catheter 12. The shape of the rounded most distal point of the obturator 28 is even more preferably rounded as shown in FIG. 4, and described further below. However, the shape of the most distal point 54 of the obturator 28 may take any other form known in the art.

Some embodiments of the obturator 28 of the catheter insertion assembly 10 may feature a proximal bend 36 and a distal bend 38 that have the approximately the same magnitude of angle. One embodiment features a distal bend with an angle of approximately 178.5° and a proximal bend of approximately 178.5°. The angle of the proximal bend 36 is the angle between the central longitudinal axis of the obturator 28 proximal to the proximal bend 36 and the central longitudinal axis of the length of the obturator 28 between the distal 38 and proximal bends 36. The angle of the distal bend 38 is the angle between the central longitudinal axis of the length of the obturator 28 between the distal 38 and proximal bends 36 and the central longitudinal axis of the length of the obturator 28 distal to the distal bend 38. The use of a relatively wide angle such as 178.5° may facilitate the formation of smooth bends. Other embodiments may have a proximal bend that features a narrow (smaller) angle than the distal bend. Still other embodiments may feature a proximal bend that features a wider (larger) angle than the distal bend.

It is preferable that the obturator 28 be sized so that it is somewhat smaller in diameter than the needle. The obturator 28 may be 1 gauge, 1.5 gauges, 2 gauges, or 3 or more gauges smaller than the needle. An obturator 28 that is 2 gauges smaller than the needle 18 has been found to reduce catheter shavings. However, any other suitable size differential between the needle and obturator may also be used.

The magnitude of the angle of the bends may be limited by the relative gauge of the needle 18 to the gauge of the obturator 28. When the needle 18 and obturator 28 are very close in gauge, e.g., only 2 gauges different, a relatively wide obtuse angle may be preferable, e.g. 178.5°. A person of ordinary skill may calculate the possible magnitude of the bends and the distance between them based on the size differential between the inner diameter of the needle and the outer diameter of the obturator.

In embodiments in which the obturator 28 is much smaller than the needle 18, it may be advantageous for the obturator 28 to feature bends with relatively narrow (small) angles. In general, the flexibility of the obturator 28 increases as the obturator 28 is reduced in size. Also, the flexibility of the distal end 32 of the obturator 28 generally increases as the magnitude of the angle of the bends in the obturator increases and generally decreases as the magnitude of the angle of the bends decreases. When using a very small obturator 28, it may be preferable to use a distal bend with a narrow (smaller) angle so that the distal bend is sufficiently rigid to push the catheter 12 wall out of the way of the sharp distal point 24 of the needle 18.

FIG. 4 shows the distal end of another embodiment of the catheter-insertion assembly 60. The catheter 62 shown in FIG. 4 has a slightly tapered distal end 64. The needle 74 is shown protruding from the distal end 64 of the catheter 62. The needle 74 has a beveled distal end 76 and a sharp distal point 80. The beveled distal end 76 of the needle 74 also features a back bevel 78. Due to the back bevel 78, the sharp distal point 80 of the needle 74 is located along the interior wall of the needle 74 rather than the exterior wall of the needle 74. This may minimize the risk of damage to the interior surface of the catheter 62 because the sharp distal point 80 of the needle 74 is located closer to the obturator 66 than the interior surface of the catheter 62.

The embodiment of the obturator 66 shown in FIG. 4 generally has more rounded features than the embodiment shown in FIGS. 1, 2, and 3. The distal end 68 of the obturator 66 of FIG. 4 is rounded. In addition, the angles of the proximal bend 70 and the distal bend 72 of the obturator 66 of FIG. 4 generally are more smooth than the angle of the bends shown in FIGS. 1, 2, and 3. As shown in FIGS. 1, 2, and 3, the bends in the obturator 28 may form be somewhat pointed. As shown in FIG. 4, the bends 70, 72 in the distal end 68 of the obturator 66 may be smooth. These smooth bends 70, 72 may slide more easily when they contact the walls of the catheter 62, thereby preventing the obturator 66 from damaging the catheter 62. The smoothness of the bends may also allow for easier insertion into the needle 74 and catheter 62. However, embodiments with bends that are less rounded as shown in FIGS. 1, 2, and 3 may also be used.

Figure 5:
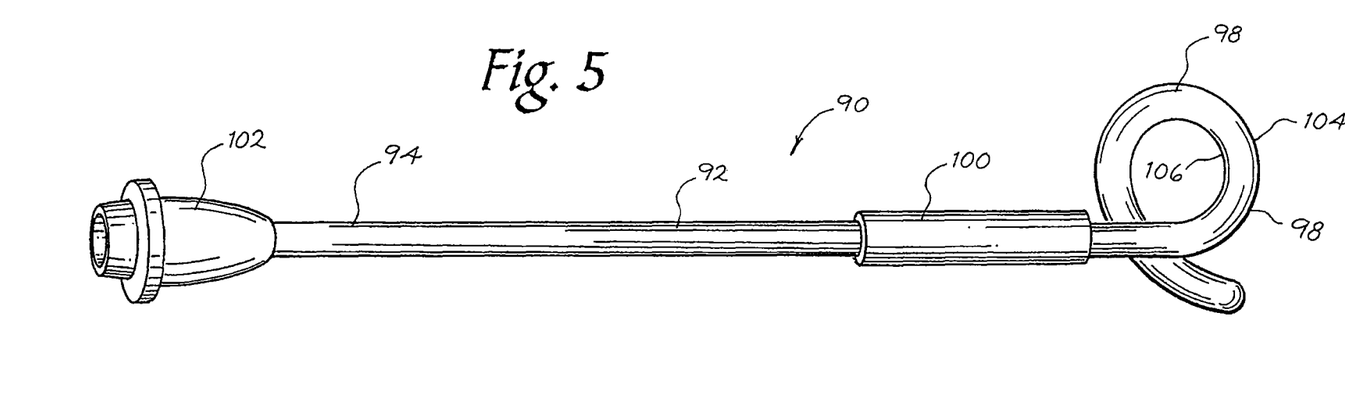
FIG. 5 is a perspective view of another embodiment of a catheter-insertion assembly.

FIG. 5 illustrates another embodiment of the catheter-insertion assembly 90 in which the distal end 98 of the catheter 92 is curved. This type of curve 92 is often called a "pigtail." As shown in FIG. 5, a piece of straight stiff tubing may be used as a pigtail straightener 100. The pigtail straightener 100 may be slid over the curved distal end 98 of the catheter 92 in order to temporarily straighten the catheter 92. This may facilitate the insertion of a needle and an obturator. Any other pigtail straightener known in the art may be used.

In embodiments having a curved distal end 98 like the embodiment shown in FIG. 5, the needle is preferably inserted into the catheter 92 so that the sharp distal point of the needle is angularly aligned with the outside of the curve 104 of the curved distal end 98 rather than along the inside of the curve 106. This minimizes the risk that the sharp most distal end of the needle will puncture or shave the catheter 92 because the needle is aligned such that the sharp most distal end runs along the portion of the catheter 92 corresponding to the widest part 104 of the curved distal end 98. After the needle has been inserted, the pigtail straightener 100 may be removed. The catheter-insertion assembly 90 will remain straight because of the needle and obturator. Once the catheter 92 is positioned in the body as desired and the needle and obturator are withdrawn, the distal end 98 of the catheter 92 will return to a curved shape. The curved distal end 98 helps to prevent the catheter 92 from migrating after insertion into a patient.

The needle may also be inserted into the catheter 92 so that the sharp distal end of the needle is aligned with the inside of the curve 106. In this embodiment, as the needle is moved distally through the catheter, the sharp distal point of the needle will naturally run across the lumen of the catheter 92 before it contacts the interior of the catheter wall. Thus, this alignment maximizes the distance the sharp distal point travels before reaching the outside bend of the catheter 92, thereby reducing the risk of damage to the catheter 92.

FIG. 5 also illustrates the use of a hub 102 at the proximal end 94 of the catheter 92. The hub 102 may be connected to the proximal end 94 of the catheter 92 through the use of a luer connection or any other method for connection known in the art. Any hub known in the art may be used. Other embodiments may omit a hub.

Figure 6:
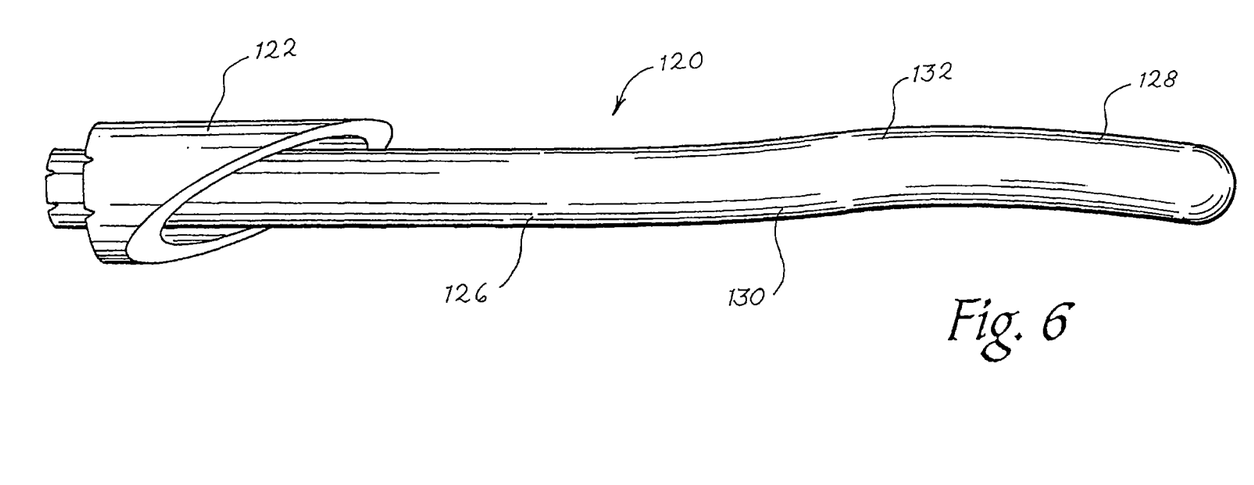
FIG. 6 is a partial perspective view of another embodiment of a catheter-insertion assembly

FIG. 6 shows another embodiment of a catheter-insertion assembly 120 with the distal end 128 of the obturator 126 protruding from the distal end 124 of the needle 122. Unlike FIG. 4, the embodiment shown in FIG. 6 does not include a needle with a back bevel. The obturator 126 of the catheter-insertion assembly 120 features very smooth, rounded bends. Thus, both the distal bend 132 and the proximal bend 130 are smooth, rounded bends. In addition, the distal bend 132 and the proximal bend 130 are angled at approximately the same degree in the opposite direction to one another.

Figure 7:
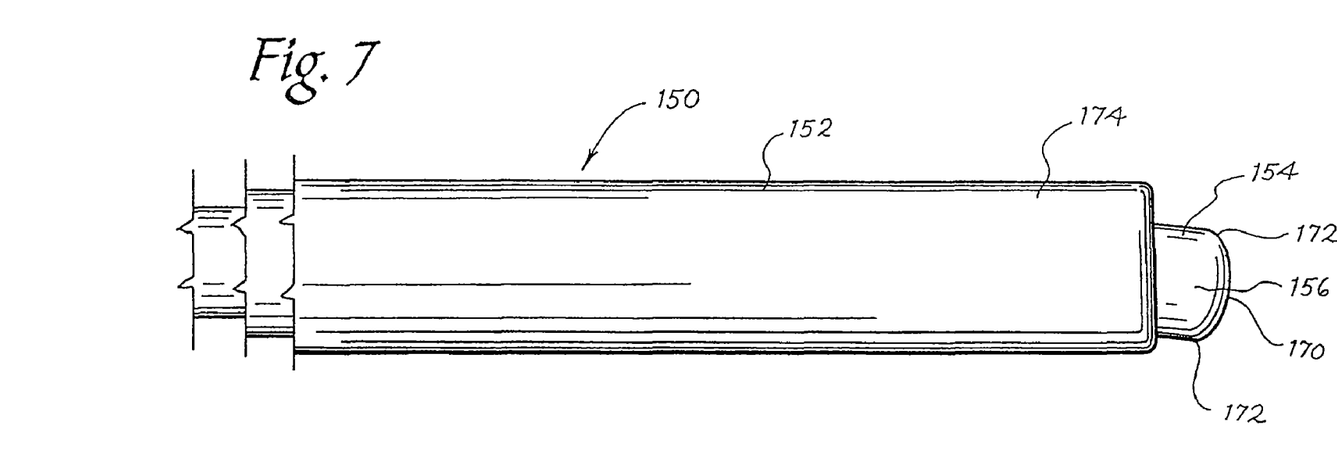
FIG. 7 is a partial perspective view of another embodiment of a catheter-insertion assembly.
Figure 8:
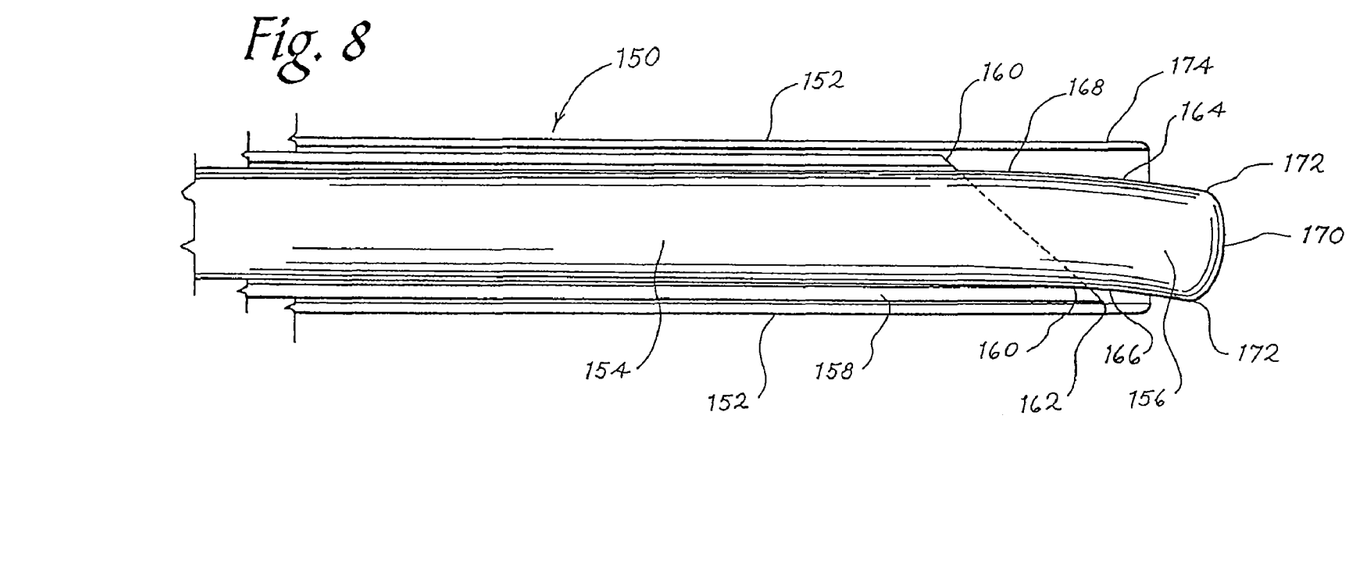
FIG. 8 is a partial side cross-sectional view of the catheter-insertion assembly of FIG. 7.

FIGS. 7 and 8 illustrate an embodiment of a catheter-insertion assembly 150 having an obturator 154 with only one bend 164. Like embodiments with a double-bend obturator, the catheter-insertion assembly 150 includes a catheter 152 having a proximal end, a distal end 174, and an interior surface. A needle 158 may be located within the catheter 152. The needle 158 has a proximal end and a beveled sharp distal end 160 forming a sharp distal point 162. The single-bend obturator 154 has a proximal end and a distal end 170. The diameter of the single-bend obturator 154 is less than the inner diameter of the needle 158 to allow the obturator 154 to be placed within the lumen of the needle 158. The obturator 154 is longer than the needle 158 to allow it to protrude distally from the sharp distal point 162 of the needle 158.

The distal end 156 of the single-bend obturator 154 features a bend 164, which has a concave side 166 and a convex side 168. The obturator 154 is preferably positioned within the needle 158 so that the concave side 166 of the bend is substantially angularly aligned with the sharp distal point 162 of the needle 158.

During use of the catheter-insertion assembly 150 with the single-bend obturator 154, the obturator 154 is preferably positioned within the needle 158 so that the bend 164 is located distal to the sharp distal point 162 of the needle 158. After being positioned in this way, the needle-obturator assembly may be slid through the lumen of a catheter 152 until the distal end 160 of the needle 158 is distal to the distal end 174 of the catheter 152. As the needle-obturator assembly is slid through the catheter 152, the rounded distal end 170 of the obturator 154 may contact the interior surface of the catheter 152 and push it slightly so that it is out of the way of the sharp distal point 162 of the needle 158. This may prevent the distal end 160 of the needle 158 from contacting the interior of the catheter 152, thereby reducing the risk of the needle 158 shaving or puncturing the catheter 152.

The location of the single bend obturator 154 may be changed relative to the needle 158 and the catheter 152 over the course of a medical procedure. It may be desirable to reposition the needle 158 and obturator 154 relative to one another and the catheter 152 in the same manner as previously described with regard to the embodiment shown in FIGS. 1, 2, and 3.

The single bend obturator may be combined with any of the features described in relation to the double bend obturator shown in FIGS. 1, 2, and 3, including a positioning mechanism for aligning the bend 164 relative to the sharp distal point 162 of the needle 158, a pigtail, a pigtail straightener, or a hub.

The components of the catheter-insertion assembly may be made from a variety of materials. The needle and obturator are preferably composed of a metal such as stainless steel or nitinol. However, the needle and the obturator may be made of any other material known in the art. The needle and obturator of an embodiment may be made from the same material or different materials. They may also be made of a combination of one or more materials. The catheter is preferably made of a material that is relatively soft and flexible. Suitable materials include polyurethane, PTFE, or any other suitable material known in the art. The catheter may also be made of any other material or combination of materials known in the art.

The rounded distal end of the obturator may vary in its shape and configuration. As shown in FIGS. 1, 2, and 3, the rounded distal end 54 of the obturator 28 may be somewhat blunt and have rounded edges 56. As shown and described in relation to FIG. 4, the obturator 66 may have a rounded distal end 68 that forms a hemisphere. FIGS. 7 and 8 illustrate another embodiment of a rounded distal end 170 of the obturator 154, which is less blunt than the embodiment shown in FIGS. 1, 2, and 3, but also not as round as the embodiment shown in FIG. 4. Like the embodiment shown in FIGS. 1, 2, and 3, this embodiment features rounded edges 172. The rounded distal end of the obturator may have any other atraumatic shape known in the art.

The angle of the bevel of the needle of the catheter insertion assembly may vary. The angle of the bevel is defined by the beveled distal end relative to the central longitudinal axis of the needle. A needle with an angle of smaller magnitude will be sharper than a needle with an angle of larger magnitude. It is preferable that the magnitude of the angle of the beveled distal end of the needle be between 12° and 35°. Although it is preferable that the angle of the beveled distal end of the needle be between 12° and 35°, any other angle of needle known in the art may be used.

The following test results demonstrated that the use of single-bend and double-bend obturators resulted in catheter shavings 50% or less of the time. The magnitude of the angles of the bends in the obturators tested was greater than approximately 170°. "Yes" denotes that at least one catheter shaving was produced in a trial. "No" denotes that no shavings were produced. All shavings were relatively small—none were visible with the naked eye. Thus, the tests produced a low occurrence of shavings and when shavings were produced they were very small.

EXAMPLE 1

A 21 gauge obturator and 23 gauge beveled needle were used. The obturator was bent once to form an angle of approximately 177.5°. The bend was positioned approximately 2 millimeters distal to the sharp distal point of the needle. The obturator and needle were then inserted through the lumen of a catheter. The sharp distal point of the needle was positioned so that it was aligned with the outside of the curve of the catheter. After insertion, no shavings were visible with the naked eye. Shavings were spotted in three trials using 7× magnification.

| Trial # | Shaving |
|---|---|
| 1 | No |
| 2 | Yes |
| 3 | No |
| 4 | Yes |
| 5 | Yes |
| 6 | No |

EXAMPLE 2

A 21 gauge obturator and 23 gauge beveled needle were used. The needle featured a back bevel. The obturator was bent once to form an angle of approximately 177.5°. The bend was positioned approximately 2 millimeters distal to the sharp distal point of the needle. The obturator and needle were then inserted through the lumen of a catheter. The sharp distal point of the needle was positioned so that it was aligned with the outside of the curve of the catheter. After insertion, no shavings were visible with the naked eye. Shavings were spotted in three trials using 7× magnification. Only one shaving was visible in each such trial.

| Trial # | Shaving |
|---|---|
| 1 | Yes |
| 2 | Yes |
| 3 | No |
| 4 | No |
| 5 | No |
| 6 | Yes |

EXAMPLE 3

A 21 gauge obturator and 23 gauge beveled needle were used. The obturator was bent twice. The angle of the proximal bend was approximately 176° and the angle of the distal bend was approximately 172°. The proximal bend was positioned approximately 2 millimeters distal to the sharp distal point of the needle. The obturator and needle were then inserted through the lumen of the catheter. The sharp distal point of the needle was positioned so that it was aligned with the outside of the curve of the catheter. After insertion, no shavings were visible with the naked eye. Shavings were spotted in two trials using 7× magnification. Only one shaving was visible in each such trial.

| Trial # | Shaving |
|---|---|
| 1 | No |
| 2 | Yes |
| 3 | No |
| 4 | Yes |
| 5 | No |
| 6 | No |

EXAMPLE 4

A 21 gauge obturator and 23 gauge beveled needle were used. The needle featured a back bevel. The obturator was bent twice. The angle of the proximal bend was approximately 176° and the angle of the distal bend was approximately 172°. The proximal bend was positioned approximately 2 millimeters distal to the sharp distal point of the needle. The obturator and needle were then inserted through the lumen of a catheter. The sharp distal point of the needle was positioned so that it was aligned with the outside of the curve of the catheter. After insertion, no shavings were visible with the naked eye. Shavings were spotted using 7× magnification. Only one such shaving was visible in each such trial.

| Trial # | Shaving |
|---------|---------|
| 1 | No |
| 2 | Yes |
| 3 | Yes |
| 4 | No |
| 5 | Yes |
| 6 | No |

Additional experiments performed with a reshaped catheter showed an even lower occurrence of shavings. A reshaped catheter is a catheter that has been previously straightened and then re-curved. In contrast, a catheter with its original curve that has not previously been straightened is not a reshaped catheter. Additional tests showed that the use of a single-bend obturator with a reshaped catheter produced a shaving in only one of six tests. Accordingly, it may be preferable to use a reshaped catheter. However, catheters that have not previously been straightened for the insertion of a needle may also be used.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A catheter-insertion assembly, said assembly comprising:
   a catheter having a proximal end, a distal end and an inner lumen extending from said proximal end to said distal end;
   a needle having a proximal end and a beveled distal end forming a sharp distal point, said needle also having a length and an inner lumen having an inner diameter; and
   wherein said needle is positioned within said lumen of said catheter;
   an obturator having a proximal end and a distal end, said obturator having a diameter that is smaller than said inner diameter of said needle, and a length that is greater than said length of said needle, said obturator having a proximal portion and a distal portion in said distal end, said proximal portion and said distal portion being disposed oppositely along a single plane;
   wherein said obturator is slidably disposed within said lumen of said needle, said obturator being movable from a retracted position in which said proximal portion and said distal portion are disposed proximal of said beveled distal end of said needle; and
   wherein said obturator is movable to an extended position in which said distal portion is disposed distal of said beveled distal end of said needle such that said distal portion extends radially outward of an outer surface of said needle and contacts an inner surface of said catheter, thereby spacing said sharp distal point of said needle radially inward of said inner surface of said catheter, said proximal portion of said obturator being biased against said inner diameter of said needle and said distal portion of said obturator being biased against said inner surface of said catheter in said extended position.

2. The catheter-insertion assembly of claim 1, wherein said proximal portion in said distal end of said obturator includes a concave side and a convex side, and said obturator is positioned such that said concave side of said proximal portion is substantially angularly aligned with said sharp distal point of said beveled distal end of said needle.

3. The catheter-insertion assembly of claim 1, wherein said obturator is sized approximately two gauges smaller than said needle.

4. The catheter-insertion assembly of claim 1, wherein said distal end of said catheter is curved.

5. The catheter-insertion assembly of claim 4 further comprising a pigtail straightener.

6. The catheter-insertion assembly of claim 1, wherein said obturator is metal.

7. The catheter-insertion assembly of claim 1, wherein the distance between said proximal portion and said distal portion in said distal end of said obturator is approximately equal to said diameter of said inner lumen.

8. The catheter-insertion assembly of claim 1, wherein said proximal portion in said distal end of said obturator is positioned approximately 2 millimeters distally from said sharp distal point of said beveled distal end of said needle.

9. The catheter-insertion assembly of claim 8, wherein said distal portion in said distal end of said obturator is positioned approximately 3.5 millimeters distally from said sharp distal point of said beveled distal end of said needle.

10. The catheter-insertion assembly of claim 1, wherein said beveled distal end of said needle includes a back bevel.

11. The catheter-insertion assembly of claim 2, further comprising a means for positioning said obturator within said needle such that said concave side of said proximal portion of said obturator is substantially angularly aligned with said sharp distal point of said needle.

12. The catheter-insertion assembly of clam 1, further comprising:
   a notch in said proximal end of said needle;
   a tab on said proximal end of said obturator, wherein said tab is sized to fit inside said notch, and said notch and tab are positioned so that when said tab is fit inside said notch, said concave side of said proximal portion of said obturator is substantially angularly aligned with said sharp distal point of said needle.

13. The catheter-insertion assembly of claim 1, wherein the length of said obturator between said distal portion and a rounded most distal point is approximately 0.5 millimeters.

14. The catheter-insertion assembly of claim 1, wherein an magnitude of the angle forming said proximal portion is substantially the same as the magnitude of an angle forming said distal portion.

15. The catheter-insertion assembly of claim 14, wherein the magnitude of the angle forming said proximal portion is approximately 178.5° and the magnitude of the angle forming said distal portion is approximately 178.5°.

* * * * *